US010060938B2

(12) United States Patent
Evers et al.

(10) Patent No.: US 10,060,938 B2
(45) Date of Patent: Aug. 28, 2018

(54) COMPACT HIGH VOLUME ANALYTICAL INSTRUMENT ARCHITECTURE

(71) Applicant: Siemens Healthcare Diagnostics Inc., Tarrytown, NY (US)

(72) Inventors: Timothy P. Evers, Wilmington, DE (US); Gregory D. Ariff, Newark, DE (US); Edward A. Nuzzaci, Lincoln University, PA (US); Edward F. Farina, Lincoln University, PA (US)

(73) Assignee: Siemens Healthcare Diagnotics Inc., Tarrytown, NY (US)

( * ) Notice: Subject to any disclaimer, the term of this patent is extended or adjusted under 35 U.S.C. 154(b) by 0 days.

(21) Appl. No.: 15/027,683

(22) PCT Filed: Oct. 15, 2014

(86) PCT No.: PCT/US2014/060751
§ 371 (c)(1),
(2) Date: Apr. 6, 2016

(87) PCT Pub. No.: WO2015/057877
PCT Pub. Date: Apr. 23, 2015

(65) Prior Publication Data
US 2016/0245835 A1 Aug. 25, 2016

Related U.S. Application Data

(60) Provisional application No. 61/892,341, filed on Oct. 17, 2013.

(51) Int. Cl.
G01N 1/38 (2006.01)
G01N 35/02 (2006.01)
(Continued)

(52) U.S. Cl.
CPC ............. *G01N 35/025* (2013.01); *G01N 1/38* (2013.01); *G01N 21/25* (2013.01); *G01N 21/76* (2013.01);
(Continued)

(58) Field of Classification Search
CPC ............... G01N 2035/0455; G01N 2035/0458
See application file for complete search history.

(56) References Cited

U.S. PATENT DOCUMENTS 4,808,380 A 2/1989 Minekane
4,908,186 A * 3/1990 Sakamaki ............ G01N 35/025
422/64

(Continued)

FOREIGN PATENT DOCUMENTS

CN 1826218 A 8/2006
CN 101424694 A 5/2009
(Continued)

OTHER PUBLICATIONS

PCT International Search Report and Written Opinion dated Dec. 19, 2014 (8 Pages).
(Continued)

Primary Examiner — Patricia Kathryn Wright

(57) ABSTRACT

An analytical instrument architecture provides high analytical test throughput in a compact footprint. A dilution section creates dilutions of a sample, a reaction processing section contains containers for assay reaction and measurement, and a reagent storage section supports reagent storage and supply. Transfer probes move the dilution and reagents to reaction containers. The dilution processing section includes concentric, independently driven rings of dilution containers; the reaction processing section includes concentric rings of reaction containers driven by the same mechanism for parallel processing of assays.

11 Claims, 3 Drawing Sheets

(51) Int. Cl.
    *G01N 35/04*     (2006.01)
    *G01N 35/10*     (2006.01)
    *G01N 21/25*     (2006.01)
    *G01N 21/76*     (2006.01)
    *G01N 27/333*     (2006.01)
    *G01N 35/00*     (2006.01)

(52) U.S. Cl.
    CPC ..... *G01N 27/333* (2013.01); *G01N 35/00871* (2013.01); *G01N 35/04* (2013.01); *G01N 35/1065* (2013.01); *G01N 2001/386* (2013.01); *G01N 2035/0441* (2013.01); *G01N 2035/0443* (2013.01); *G01N 2035/0444* (2013.01); *G01N 2035/0448* (2013.01); *G01N 2035/0453* (2013.01); *G01N 2035/0458* (2013.01)

(56) References Cited

U.S. PATENT DOCUMENTS

| | | |
|---|---|---|
| 5,270,211 A | 12/1993 | Kelln |
| 6,146,592 A | 11/2000 | Kawashima et al. |
| 6,319,718 B1 | 11/2001 | Matsubara et al. |
| 6,924,152 B2 | 8/2005 | Matsubara et al. |
| 7,105,351 B2 | 9/2006 | Matsubara et al. |
| 7,897,337 B2 | 3/2011 | Macioszek et al. |
| 8,158,058 B2 | 4/2012 | Shiba et al. |
| 2005/0013737 A1* | 1/2005 | Chow .................. G01N 35/025 422/63 |
| 2009/0068748 A1* | 3/2009 | Komatsu .......... G01N 35/00584 436/43 |
| 2011/0256629 A1* | 10/2011 | Wang ................. G01N 35/1002 436/45 |

FOREIGN PATENT DOCUMENTS

| | | |
|---|---|---|
| CN | 102830238 A | 12/2012 |
| JP | H04 47267 A | 2/1992 |

OTHER PUBLICATIONS

Extended EP Search Report dated Sep. 20, 2016 of corresponding European Application No. 14853979.4, 4 Pages.

\* cited by examiner

COMPACT HIGH VOLUME ANALYTICAL INSTRUMENT ARCHITECTURE

CROSS-REFERENCE TO RELATED APPLICATIONS

This application claims priority to U.S. provisional application Ser. No. 61/892,341 filed Oct. 17, 2013, which is incorporated herein by reference in its entirety.

TECHNOLOGY FIELD

The present invention relates generally to an instrument architecture for an automatic analyzer and, more particularly, to an instrument architecture design that provides a high analytical test throughput in a compact footprint.

BACKGROUND

As automatic analyzers handle multitudes of samples, there is a need for high throughput. Customers would like to handle larger volumes of tests with instruments that have a smaller footprint in order to minimize space requirements. In general, high test throughput in a small footprint is an attractive feature.

Traditionally, throughput has been increased by reducing instrument cycle time. Reduced cycle times result in less robust operation of the analyzer.

Thus, there is a need for an instrument architecture design for an automatic analyzer that provides a high analytical test throughput in a compact footprint without reducing cycle time.

SUMMARY

Some embodiments are directed to an instrument architecture design that provides a high analytical test throughput in a compact footprint. Exemplary embodiments disclosed herein disclose an architecture that provides increased throughput within the footprint of an existing instrument or a slight increase in footprint with a small increase in parts. For example, in some embodiments, twice or near twice the throughput is provided within the footprint of an existing instrument. In other embodiments, twice or near twice the throughput is provided with a slight increase in footprint and with an approximately 60% increase in parts.

The compact high volume analytical instrument architecture comprises a dilution section to create one or more pre-diluted aliquots of an incoming sample, a reaction processing section containing cuvettes or containers in which an assay reaction and measurement are conducted, and a reagent storage section supporting storage of the reaction reagents and supply to the reaction cuvette. Transfer probes to move the pre-diluted sample and reagents to the reaction cuvette, along with mixers, cuvette washers, photometers, and other components to support processing of the assay, are also included. In some embodiments, an ion-selective electrode (ISE) section to measure electrolytes is also provided.

In one embodiment, the dilution processing section is comprised of two concentric and independently driven rings of dilution cuvettes (also referred to as aliquot vessels or containers) forming a rotating stream of vessels. The dilution process is supported by mixers and vessel washers associated with each of the rings (also referred to as streams). One or more dilution probes access the vessels or containers on either of the rings or streams to create a pre-dilution for later processing by the reaction processing section.

In one embodiment, the reaction processing section is comprised of two concentric rings of reaction cuvettes or containers (reaction rings) driven by the same drive mechanism so that they move together and provide two streams for the parallel processing of assays. The reaction rings index in a pre-defined pattern to present each individual reaction cuvette to supporting resources positioned around each ring at the appropriate time. These resources transfer sample and reagent from their respective sources and also mix and measure the reaction as well as clean the reaction cuvette for re-use after processing.

In one embodiment, the reagent storage section is comprised of two reagent storage areas supporting storage of the reaction reagents and supply to the reaction cuvette. One area supports reagents for a first reagent addition and the other for a second reagent addition. Each area includes two concentric and independently driven rings to support the respective reagent for each of two processing rings or streams. Separate reagent transfer probes are used to independently transfer reagent from each ring to the reaction cuvette or container for their respective reaction processing stream.

The ISE system is comprised of an independent dilution probe to create a dilution of patient sample in the ISE port. The diluted sample is drawn from the ISE port into the ISE system for measurement.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION

Embodiments are directed to an analytical instrument architecture design that provides a high analytical test throughput in a compact footprint. Although embodiments provided herein are described with respect to a particular number of rings, probes, and processing rings or streams, the architecture is not so limited. Instead, the architecture may include additional rings, probes, and processing streams.

Figure 1:
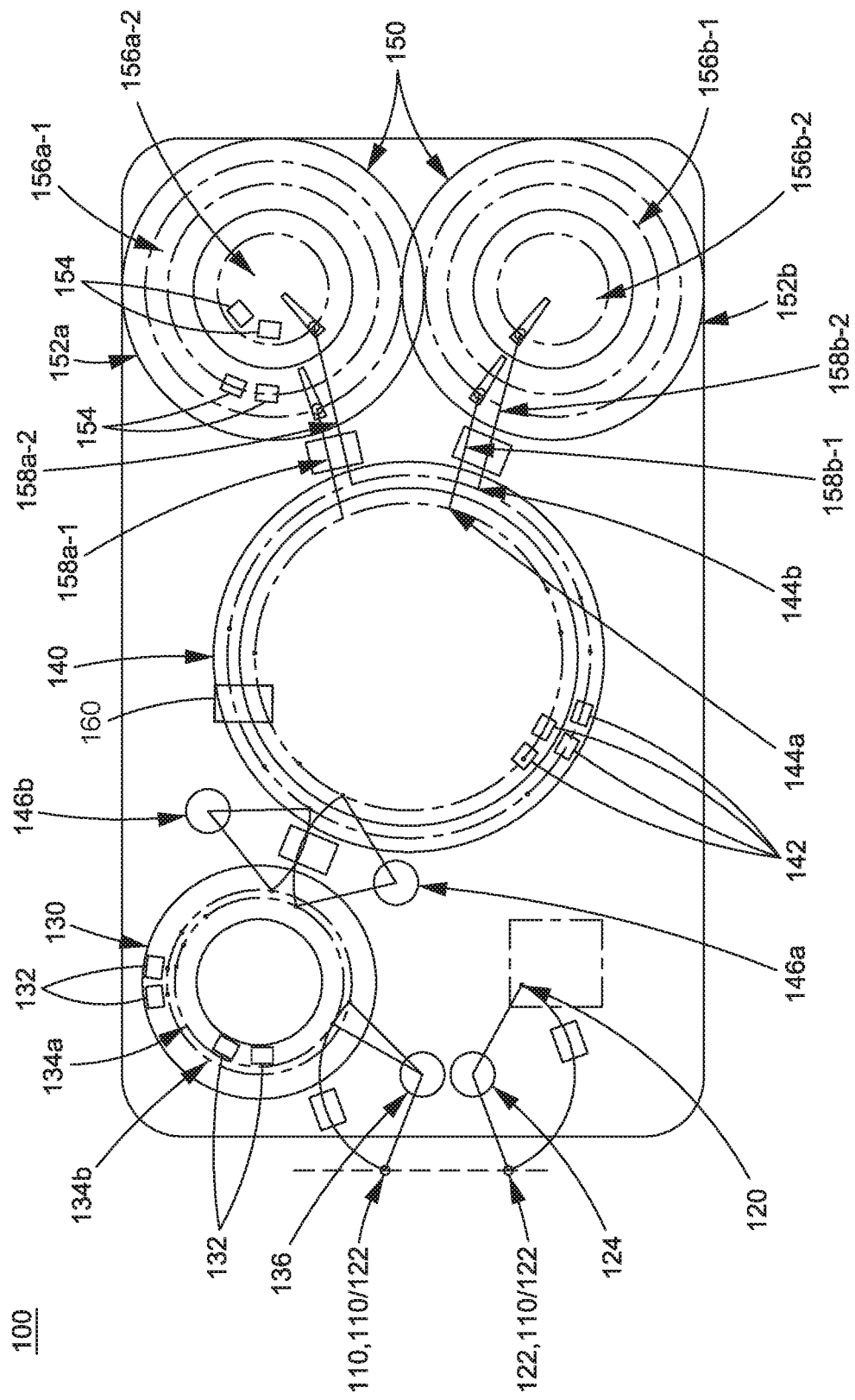
FIG. 1 is a layout of an exemplary system architecture, according to an embodiment.

FIG. 1 provides a layout of an exemplary system architecture 100.

As shown in FIG. 1, access position 110 provides access to a patient sample.

Also shown in FIG. 1 are an ion-selective electrode (ISE) port 120, an ISE access position 122 for access of the sample to the ISE port 120, and an ISE diluting probe 124 for transferring the sample from the ISE access position 122 and creating a dilution in the ISE port 120.

According to an embodiment, a diluting turntable 130 is comprised of a plurality of diluting containers 132 arranged in a plurality of diluting rings 134. Shown are two diluting rings 134a and 134b, but the invention is not limited to two diluting rings 134. In an embodiment, the diluting rings 134 are concentric and independently-driven and controllable with respect to one another. A diluting probe 136 transfers sample from the access position 110 to one or more of the plurality of diluting containers 132 to create a dilution therein. The transfer of sample from the access position 110 by the diluting probe 136 may be to one or more diluting containers 132 on any of the plurality of diluting rings 134.

With continued reference to FIG. 1, a reaction turntable 140 includes a plurality of reaction containers 142 arranged in a plurality of reaction rings 144a, 144b, the reaction rings 144a, 144b being concentric and, according to an embodiment, operating in parallel with respect to one another. For example, the plurality of reaction rings 144a, 144b may be driven by the same drive mechanism 160 so that they move together and provide two processing paths for the parallel processing of assays. A plurality of sample transfer probes 146a, 146b are provided, each sample transfer probe 146a, 146b dedicated to a respective one of the plurality of reaction rings 144a, 144b. Shown in FIG. 1 are the two reaction rings 144a and 144b with respective dedicated sample transfer probes 146a and 146b; however, the invention is not limited to two reaction rings and two sample transfer probes.

The sample transfer probes 146 transfer the dilution from the one or more of the plurality of diluting containers 132 on any of the plurality of diluting rings 134 to one or more of the plurality of reaction containers 142 on the respective one of the plurality of reaction rings 144. That is, the sample transfer probe 146a may transfer the dilution from any of the diluting containers 132 to one or more reaction containers 142 on the reaction ring 144a, while the sample transfer probe 146b transfer the dilution to the reaction ring 144b. In an embodiment, the plurality of sample transfer probes 146 are independently-driven and controllable with respect to one another.

A reagent storage section 150 is, according to an embodiment, comprised of a plurality of reagent storage areas 152, each of the plurality of reagent storage areas 152 dedicated to storage and supply of a respective reagent. Each reagent storage area 152 includes a plurality of reagent containers 154 arranged in a plurality of reagent rings 156. In an embodiment, in each reagent storage area 152, the respective reagent rings 156 are concentric and independently-driven and controllable with respect to one another. Moreover, each reagent ring 156 is dedicated to a respective one of the plurality of reaction rings 144.

A plurality of reagent transfer probes 158 are provided, each reagent transfer probe 158 dedicated to a respective one of the plurality of reagent rings 156 for transferring a reagent from one or more of the plurality of reagent containers 154 on the respective one of the plurality of reagent rings 156 to one or more of the plurality of reaction containers 142 on a corresponding one of the plurality of reaction rings 144. In an embodiment, the plurality of reagent transfer probes 158 are independently-driven and controllable with respect to one another.

Thus, for example as shown in FIG. 1, for two reagents, Reagent A and Reagent B, there are two reagent storage areas 152a and 152b, where 152a is dedicated to Reagent A and 152b is dedicated to Reagent B. Each reagent storage area 152a and 152b has two reagent rings 156a-1, 156a-2 and 156b-1, 156b-2, respectively, to correspond to the two reaction rings 144a and 144b. Additionally, for two reagents, Reagent A and Reagent B, there are four reagent transfer probes 158a-1, 158a-2 and 158b-1, 158b-2. Reagent transfer probe 158a-1 is dedicated to reagent ring 156a-1 for transferring Reagent A from a reagent container 154 on reagent ring 156a-1 to one or more reaction containers 142 on reaction ring 144a; reagent transfer probe 158a-2 is dedicated to reagent ring 156a-2 for transferring Reagent A from a reagent container 154 on reagent ring 156a-2 to one or more reaction containers 142 on reaction ring 144b; reagent transfer probe 158b-1 is dedicated to reagent ring 156b-1 for transferring Reagent B from a reagent container 154 on reagent ring 156b-1 to one or more reaction containers 142 on reaction ring 144a; and reagent transfer probe 158b-2 is dedicated to reagent ring 156b-2 for transferring Reagent B from a reagent container 154 on reagent ring 156b-2 to one or more reaction containers 142 on reaction ring 144b. This description of two reagents is provided as an example and is not a limitation; additional reagents may be handled by the architecture 100, resulting in an increase in reagent storage areas 152.

Additionally, the system architecture 100 includes a controller for controlling operation of the various components, including the probes, the turntables, and the rings.

I. Dilution Processing Operation:

The architecture 100, according to an embodiment, provides for two concentric diluting rings 134a and 134b, driven independently, each with, according to an embodiment, dedicated mixers and wash stations.

A single diluting probe 136 makes dilutions in either of both diluting rings 134a and 134b from patient sample, accessed at access position 110. According to an embodiment, only a single dilution will be made in one of the two rings 134a, 134b on each dilution probe cycle.

An optional separate diluting probe, ISE diluting probe 124, is dedicated to transferring and diluting samples from the ISE access position 122 to the ISE port 120.

According to an embodiment, two sample transfer probes 146a and 146b are provided, each one dedicated to serving one of the two reaction rings 144a and 144b, respectively. However, both sample transfer probes 146a and 146b can reach both diluting rings 134a and 134b according to the scheme described below.

According to an embodiment, during synchronous diluting ring operation (in which the diluting rings 134a and 134b move with a defined indexing scheme and dilutions, mixes, and washes are performed), each diluting ring 134a and 134b will have a dedicated sample transfer probe 146a and 146b. This ties each diluting ring 134a and 134b to one of the two reaction rings 144a and 144b during synchronous operation only.

According to an embodiment, during asynchronous diluting ring operation (in which the diluting ring 134a or 134b moves to provide any dilution to be sampled, and dilutions, mixes, and washes are not performed), either sample transfer probe 146a or 146b can access the diluting ring 134a or 134b, though not during the same machine cycle.

During asynchronous operation with the non-dedicated sample transfer probe 146a or 146b, diluting container 132 alignments may be offset slightly from that during the synchronous operation. In other words, when the non-dedicated sample transfer probe 146a or 146b is accessing a diluting container 132, containers 132 may not line up accurately under the mixers and washers. This is of no consequence since no dilutions, mixes, or washes occur during asynchronous operation.

Since, according to an embodiment, the diluting probe 136 makes dilutions into one of the two diluting rings 134a or 134b during a single cycle, only one of the two diluting rings 134a or 134b operate synchronously during a given machine cycle. An exception may occur where, for example, it is desired to perform mixes and washes but not dilutions on the other ring 134a or 134b. However, both diluting rings 134a and 134b may operate asynchronously at the same time.

When a diluting ring 134a and/or 134b returns to synchronous mode after running asynchronously, it goes to the next step in the synchronous cycle from where it left off. For example, the diluting container 132 which last received a dilution will go to the mix station. In synchronous mode, a new (never before sampled) dilution is always presented to the respective dedicated sample transfer probe 146a or 146b.

The benefits for the scheme include: Only a single dilution (for each dilution concentration) needs to be made (rather than one in each diluting ring 134a and 134b), since the diluting ring 134a and 134b is available to both sample transfer probes 146a and 146b and, hence, both reaction rings 144a and 144b and reagent sets; with each sample transfer probe 146a and 146b dedicated to a single reaction ring 144a and 144b, differences in sample probe performance will calibrate out (it may, according to an embodiment, be necessary to calibrate methods on each reaction ring 144a and 144b independently due also to separate photometers, reagent probes, etc.); with one diluting ring 134a or 134b running synchronously and the other asynchronously, the throughput of the diluting probe 136 and sample deliveries become independent (assuming that tests are available to run on the appropriate photometric channels for each diluting/reaction ring pair).

Figure 2:
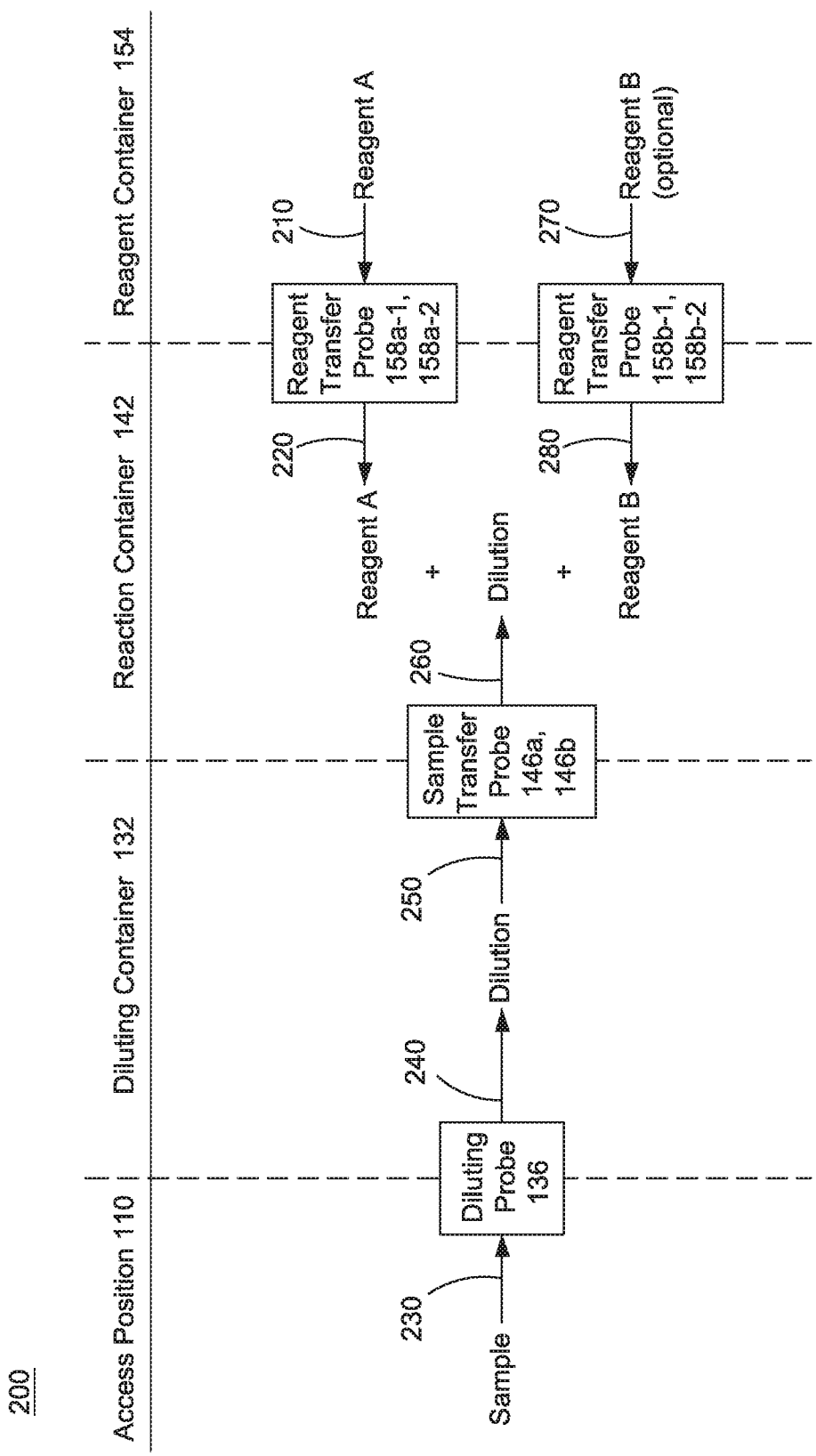
FIG. 2 is a flow diagram illustrating a method for processing a reaction using the exemplary system architecture according to embodiments provided herein.

II. Reaction Ring Operation:

According to an embodiment, assay processing is performed on each of two reaction rings 144a and 144b simultaneously. As an example, and with reference to the flow diagram of FIG. 2, an assay is processed in the following steps:

A measured amount of a first reagent (Reagent A) is added to an empty reaction container 142 at time 0 (Reagent A is transferred from a reagent container (210) via a reagent transfer probe 158a-1 or 158a-2 to a reaction container on reaction ring 144a or 144b, respectively; (220)).

At some fixed later time (e.g., about 3 to about 60 seconds later) a measured amount of pre-diluted sample is added to the reaction container followed by mixing of the reaction container at a following index (diluting probe 136 transfers a sample from the access position 110 (230) to a diluting container (240) on a diluting ring 134a or 134b; a sample transfer probe 146a or 146b transfers the dilution from the diluting container (250) to the reaction container (260) on reaction ring 144a or 144b).

For some assays, only one reagent (e.g., Reagent A) is required to perform the analysis. For other assays, a second reagent (e.g., Reagent B) is added at a fixed time after sample addition followed by a mix. Typically this time ranges from about 200 to about 300 seconds after sample addition (Reagent B is transferred from a reagent container (270) via a reagent transfer probe 158b-1 or 158b-2 to a reaction container on reaction ring 144a or 144b, respectively (280)).

Although the timing for sample and reagent additions can vary from system to system, in the exemplary architecture 100, according to an embodiment, these additions occur at fixed points in time that are the same for all assays.

In an embodiment, the absorbance of the reaction container 142 is read by a photometer throughout the reaction process. Results may calculated from absorbance measurements made at pre-selected points in time. For the system 100 described, these points can be different dependent upon the needs of the specific assay being conducted.

In an embodiment, the architecture 100 also includes a detector configured to measure a reaction in the reaction container. The detector may comprise one or more photometric detectors arranged to measure the absorbance of the reaction in the reaction container. In an embodiment, the reaction container is moved from its position on a reaction ring 144a or 144b to another location for measurement by a detector. n an embodiment, the detector comprises a luminometer.

Each assay (reaction) ring or "stream" 144a and 144b is serviced by a dedicated sample transfer probe 146a and 146b as described above in the Dilution Processing Operation section.

Each assay (reaction) ring or "stream" 144a and 144b is serviced by two dedicated reagent transfer probes 158a-1, 158b-1 and 158a-2, 158b-2, respectively, to transfer reagents (Reagent A and, if needed, Reagent B) from the respective reagent storage area to the reaction container associated with that ring "stream."

III. Reagent Storage Operation

According to an embodiment, the reagent storage section 150 is comprised of two reagent storage areas 152a and 152b, supporting storage of the reaction reagents for supply to the reaction containers 142. One area provides the supply for the first reagent used for both reaction rings 144a and 144b, and the other for the second reagent used by both reaction rings 144a and 144b. For example, reagent storage area 152a may, according to an embodiment, provide Reagent A to reaction rings 144a and 144b, while reagent storage area 152b provides Reagent B to the reaction rings 144a and 144b.

According to an embodiment, each storage area 152a and 152b is comprised of two concentric and independently driven rings to support the respective reagent for each of two processing "streams" (156a-1 and 156a-2 for Reagent A in storage area 152a, and 156b-1 and 156b-2 for Reagent B in storage area 152b).

Separate reagent transfer probes (158a-1 and 158a-2, and 158b-1 and 158b-2) are used to independently transfer reagent from each ring to the reaction container for their respective reaction processing "stream". For example, according to an embodiment, 158a-1 transfers Reagent A stored in reagent ring 156a-1 to the reaction containers in reaction ring or "stream" 144a.

IV. ISE System Operation

According to an embodiment, the ISE system is comprised of an independent ISE diluting probe 124 to create a dilution of patient sample in the ISE port 120. The diluted sample is drawn from the ISE port into the ISE system for measurement. In an embodiment, the ISE system operates independently of the rest of the architecture 100 described above and is an optional feature of the architecture 100.

In one embodiment, the access position 110 and the ISE access position 122 comprise the same physical location (either location 110, 110/122 or location 122, 110/122). In this case, the diluting probe 136 and the ISE diluting probe 124 may alternate turns for accessing the sample.

Figure 3:
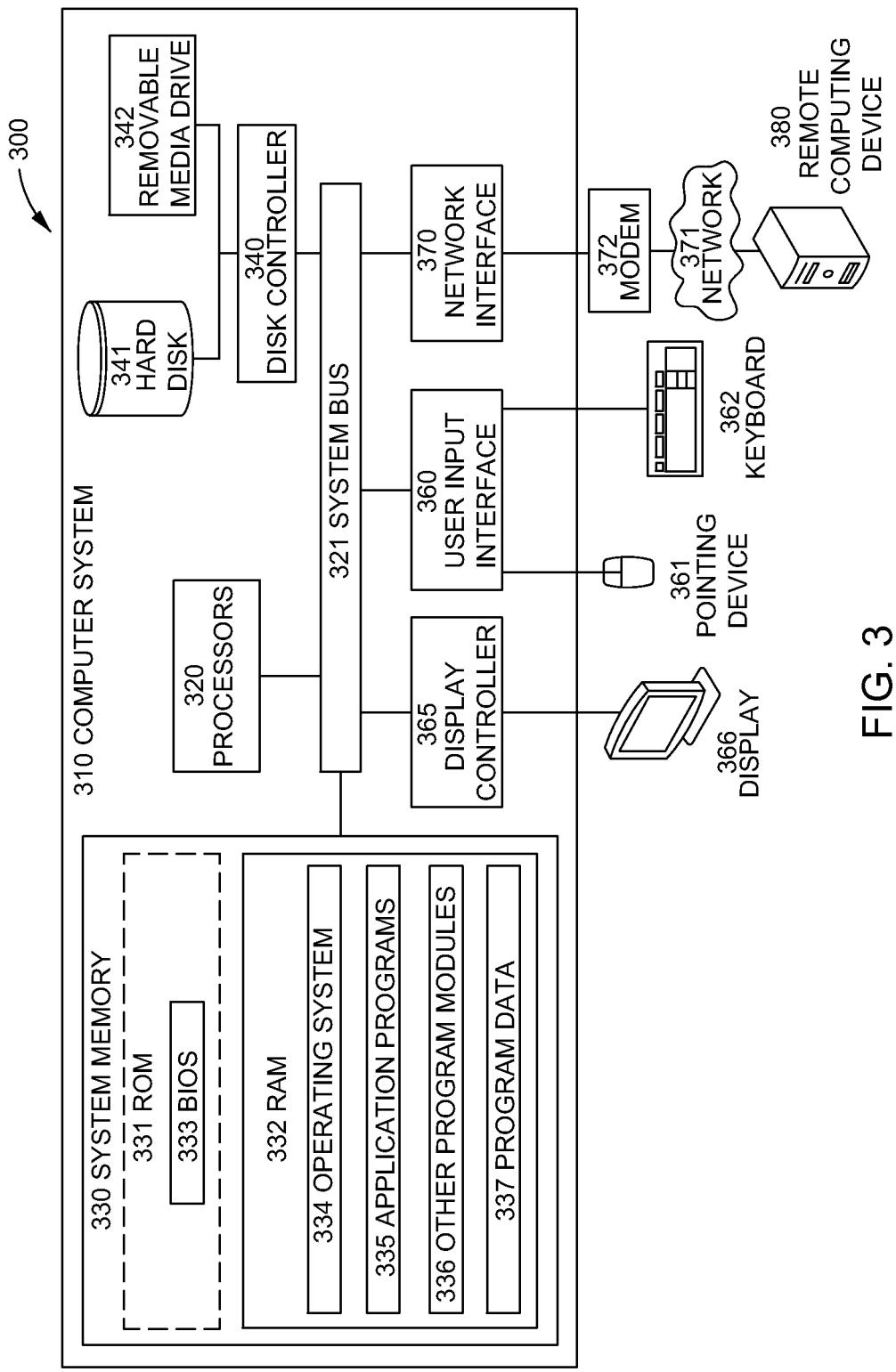
FIG. 3 illustrates an exemplary computing environment within which embodiments of the invention may be implemented.

FIG. 3 illustrates an exemplary computing environment 300 within which embodiments of the invention may be implemented. Computing environment 300 may include computer system 310, which is one example of a general purpose computing system upon which embodiments of the invention may be implemented. Computers and computing environments, such as computer 310 and computing environment 300, are known to those of skill in the art and thus are described briefly here.

As shown in FIG. 3, the computer system 310 may include a communication mechanism such as a bus 321 or other communication mechanism for communicating information within the computer system 310. The system 310 further includes one or more processors 320 (such as the controller described above, configured to control operation of the various components, including the probes, the turntables, and the rings) coupled with the bus 321 for processing the information. The processors 320 may include one or more central processing units (CPUs), graphical processing units (GPUs), or any other processor known in the art.

The computer system 310 also includes a system memory 330 coupled to the bus 321 for storing information and instructions to be executed by processors 320. The system memory 330 may include computer readable storage media in the form of volatile and/or nonvolatile memory, such as read only memory (ROM) 331 and/or random access memory (RAM) 332. The system memory RAM 332 may include other dynamic storage device(s) (e.g., dynamic RAM, static RAM, and synchronous DRAM). The system memory ROM 331 may include other static storage device(s) (e.g., programmable ROM, erasable PROM, and electrically erasable PROM). In addition, the system memory 330 may be used for storing temporary variables or other intermediate information during the execution of instructions by the processors 320. A basic input/output system (BIOS) 333 containing the basic routines that help to transfer information between elements within computer system 310, such as during start-up, may be stored in ROM 331. RAM 332 may contain data and/or program modules that are immediately accessible to and/or presently being operated on by the processors 320. System memory 330 may additionally include, for example, operating system 334, application programs 335, other program modules 336 and program data 337.

The computer system 310 also includes a disk controller 340 coupled to the bus 321 to control one or more storage devices for storing information and instructions, such as a magnetic hard disk 341 and a removable media drive 342 (e.g., floppy disk drive, compact disc drive, tape drive, and/or solid state drive). The storage devices may be added to the computer system 310 using an appropriate device interface (e.g., a small computer system interface (SCSI), integrated device electronics (IDE), Universal Serial Bus (USB), or FireWire).

The computer system 310 may also include a display controller 365 coupled to the bus 321 to control a display or monitor 366, such as a cathode ray tube (CRT) or liquid crystal display (LCD), for displaying information to a computer user. The computer system 310 includes an input interface 360 and one or more input devices, such as a keyboard 362 and a pointing device 361, for interacting with a computer user and providing information to the processors 320. The pointing device 361, for example, may be a mouse, a trackball, or a pointing stick for communicating direction information and command selections to the processors 320 and for controlling cursor movement on the display 366. The display 366 may provide a touch screen interface which allows input to supplement or replace the communication of direction information and command selections by the pointing device 361.

The computer system 310 may perform a portion or all of the processing steps of embodiments of the invention in response to the processors 320 executing one or more sequences of one or more instructions contained in a memory, such as the system memory 330. Such instructions may be read into the system memory 330 from another computer readable medium, such as a hard disk 341 or a removable media drive 342. The hard disk 341 may contain one or more data-stores and data files used by embodiments of the present invention. Data-store contents and data files may be encrypted to improve security. The processors 320 may also be employed in a multi-processing arrangement to execute the one or more sequences of instructions contained in system memory 330. In alternative embodiments, hard-wired circuitry may be used in place of or in combination with software instructions. Thus, embodiments are not limited to any specific combination of hardware circuitry and software.

As stated above, the computer system 310 may include at least one computer readable medium or memory for holding instructions programmed according embodiments of the invention and for containing data structures, tables, records, or other data described herein. The term "computer readable medium" as used herein refers to any medium that participates in providing instructions to the processors 320 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 341 or removable media drive 342. Non-limiting examples of volatile media include dynamic memory, such as system memory 330. Non-limiting examples of transmission media include coaxial cables, copper wire, and fiber optics, including the wires that make up the bus 321. Transmission media may also take the form of acoustic or light waves, such as those generated during radio wave and infrared data communications.

The computing environment 300 may further include the computer system 310 operating in a networked environment using logical connections to one or more remote computers, such as remote computer 380. Remote computer 380 may be a personal computer (laptop or desktop), a mobile device, a server, a router, a network PC, a peer device or other common network node, and typically includes many or all of the elements described above relative to computer system 310. When used in a networking environment, computer system 310 may include modem 372 for establishing communications over a network 371, such as the Internet. Modem 372 may be connected to system bus 321 via user network interface 370, or via another appropriate mechanism.

Network 371 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 310 and other computers (e.g., remote computing system 380). The network 371 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 871.

As described herein, the various systems, subsystems, agents, managers and processes can be implemented using hardware components, software components and/or combinations thereof.

Although the present invention has been described with reference to exemplary embodiments, it is not limited thereto. Those skilled in the art will appreciate that numerous changes and modifications may be made to the preferred embodiments of the invention and that such changes and modifications may be made without departing from the true spirit of the invention. It is therefore intended that the appended claims be construed to cover all such equivalent variations as fall within the true spirit and scope of the invention.

We claim:

1. An architecture for a compact high volume automated clinical analyzer, comprising:
    an access position for access of samples;
    a diluting turntable comprising a plurality of diluting containers arranged in a first diluting ring and a second diluting ring, the first diluting ring and the second diluting ring being concentric and independently-driven and controllable with respect to one another;
    a diluting probe for transferring sample from the access position and creating a dilution in one or more of the plurality of diluting containers on either of the first diluting ring or the second diluting ring;
    a reaction turntable comprising a plurality of reaction containers arranged in a first reaction ring and a second reaction ring, the first reaction ring and the second reaction ring being concentric and operating in parallel with respect to one another;
    a plurality of sample transfer probes comprising a first sample transfer probe and a second sample transfer probe, the first sample transfer probe being dedicated to the first reaction ring for transferring the dilution from the one or more of the plurality of diluting containers on the first diluting ring to one or more of the plurality of reaction containers on the first reaction ring, the second sample transfer probe being dedicated to the second reaction ring for transferring the dilution from the one or more of the plurality of diluting containers on the second diluting ring to one or more of the plurality of reaction containers on the second reaction ring, the plurality of sample transfer probes independently-driven and controllable with respect to one another;
    a reagent storage section comprising a plurality of reagent storage areas, each of the plurality of reagent storage areas dedicated to storage and supply of a respective reagent, each reagent storage area comprising a plurality of reagent containers arranged in a first reagent ring and a second reagent ring, the first reagent ring and the second reagent ring being concentric and independently-driven and controllable with respect to one another, wherein the first reagent ring is dedicated to the first reaction ring and the second reagent ring is dedicated to the second reaction ring;
    a plurality of reagent transfer probes comprising a first reagent transfer probe and a second reagent transfer probe, the first reagent transfer probe dedicated to the first reagent ring for transferring a reagent from one or more of the plurality of reagent containers on the first reagent ring to one or more of the plurality of reaction containers on the first reaction ring, the second reagent transfer probe dedicated to the second reagent ring for transferring a reagent from one or more of the plurality of reagent containers on the second reagent ring to one or more of the plurality of reaction containers on the second reaction ring, the plurality of reagent transfer probes independently-driven and controllable with respect to one another; and
    a controller for controlling operation of the diluting probe, the diluting turntable, the reaction turntable, the plurality of sample transfer probes, the reagent storage section, and the plurality of reagent transfer probes to provide parallel processing of assays through separate processing paths including a first processing path and a second processing path,
    wherein the first diluting ring, the first sample transfer probe, the first reaction ring, the first reagent ring, and the first reagent transfer probe are elements of the first processing path and the controller controls operation such that the elements of the first processing path are dedicated to each other,
    wherein the second diluting ring, the second sample transfer probe, the second reaction ring, the second reagent ring, and the second reagent transfer probe are elements of the second processing path and the controller controls operation such that the elements of the second processing path are dedicated to each other, and
    wherein the reaction container is moved from the corresponding one of the plurality of reaction rings to another location for measurement by a detector.

2. The architecture of claim 1, wherein the detector comprises a luminometer.

3. The architecture of claim 1, wherein one of the plurality of diluting rings operates synchronously during a given cycle.

4. The architecture of claim 1, wherein the plurality of diluting rings operate asynchronously at the same time.

5. The architecture of claim 1, wherein, when one of the plurality of diluting rings returns to synchronous operation after running asynchronously, the one of the plurality of diluting rings resumes a synchronous cycle at a previous left-off position.

6. The architecture of claim 1, wherein the transferring of the reagent and transferring of the dilution are done at fixed times with respect to one another.

7. The architecture of claim 1, further comprising:
    an ion-selective electrode (ISE) port;
    an ISE access position for access of samples to the ISE port; and
    an ISE diluting probe for transferring sample from the ISE access position and
    creating a dilution in the ISE port.

8. The architecture of claim 7, wherein the ISE port operates independently of the diluting probe, the diluting turntable, the reaction turntable, the plurality of sample transfer probes, the reagent storage section, and the plurality of reagent transfer probes.

9. The architecture of claim 7, wherein the access position and the ISE access position comprise the same physical location, and wherein the diluting probe and the ISE diluting probe alternate turns for accessing the sample.

10. The architecture of claim 1, wherein the first reagent ring and the second reagent ring are both dedicated to the same reagent.

11. An architecture for a compact high volume automated clinical analyzer, comprising:
    an access position for access of samples;

a diluting turntable comprising a plurality of diluting containers arranged in a first diluting ring and a second diluting ring, the first diluting ring and the second diluting ring being concentric and independently-driven and controllable with respect to one another;

a diluting probe for transferring sample from the access position and creating a dilution in one or more of the plurality of diluting containers on either of the first diluting ring or the second diluting ring;

a reaction turntable comprising a plurality of reaction containers arranged in a first reaction ring and a second reaction ring, the first reaction ring and the second reaction ring being concentric and operating in parallel with respect to one another;

a plurality of sample transfer probes comprising a first sample transfer probe and a second sample transfer probe, the first sample transfer probe being dedicated to the first reaction ring for transferring the dilution from the one or more of the plurality of diluting containers on the first diluting ring to one or more of the plurality of reaction containers on the first reaction ring, the second sample transfer probe being dedicated to the second reaction ring for transferring the dilution from the one or more of the plurality of diluting containers on the second diluting ring to one or more of the plurality of reaction containers on the second reaction ring, the plurality of sample transfer probes independently-driven and controllable with respect to one another;

a reagent storage section comprising a plurality of reagent storage areas, each of the plurality of reagent storage areas dedicated to storage and supply of a respective reagent, each reagent storage area comprising a plurality of reagent containers arranged in a first reagent ring and a second reagent ring, the first reagent ring and the second reagent ring being concentric and independently-driven and controllable with respect to one another, wherein the first reagent ring is dedicated to the first reaction ring and the second reagent ring is dedicated to the second reaction ring;

a plurality of reagent transfer probes comprising a first reagent transfer probe and a second reagent transfer probe, the first reagent transfer probe dedicated to the first reagent ring for transferring a reagent from one or more of the plurality of reagent containers on the first reagent ring to one or more of the plurality of reaction containers on the first reaction ring, the second reagent transfer probe dedicated to the second reagent ring for transferring a reagent from one or more of the plurality of reagent containers on the second reagent ring to one or more of the plurality of reaction containers on the second reaction ring, the plurality of reagent transfer probes independently-driven and controllable with respect to one another; and a controller for controlling operation of the diluting probe, the diluting turntable, the reaction turntable, the plurality of sample transfer probes, the reagent storage section, and the plurality of reagent transfer probes, wherein the reaction container is moved from the corresponding one of the plurality of reaction rings to another location for measurement by a detector, and wherein the first reaction ring and the second reaction ring are driven by a common drive mechanism such that the first reaction ring and the second reaction ring move together.

* * * * *